United States Patent [19]

Varma et al.

[11] Patent Number: 4,529,548
[45] Date of Patent: Jul. 16, 1985

[54] 17β-(SUBSTITUTED THIO)ANDROSTENES

[75] Inventors: Ravi K. Varma, Belle Mead; Rudiger D. Haugwitz, Titusville, both of N.J.

[73] Assignee: E. R. Squibb & Sons, Inc., Princeton, N.J.

[21] Appl. No.: 607,920

[22] Filed: May 7, 1984

[51] Int. Cl.³ ............................................. C07J 1/00
[52] U.S. Cl. .................................................. 260/397.45
[58] Field of Search ......................... 260/397.3, 397.45

[56] References Cited

U.S. PATENT DOCUMENTS

| 2,999,101 | 9/1961 | Dodson et al. | 260/397.3 |
| 4,091,036 | 5/1978 | Varma | 260/397.45 |
| 4,094,840 | 6/1978 | Varma | 260/239.55 |
| 4,133,811 | 1/1979 | Varma | 260/239.55 R |
| 4,146,538 | 5/1979 | Varma et al. | 260/239.55 R |
| 4,183,924 | 1/1980 | Green et al. | 424/242 |
| 4,265,815 | 5/1981 | Varma | 260/239.55 R |
| 4,361,559 | 11/1982 | Varma | 424/243 |
| 4,397,782 | 8/1983 | Varma | 260/239.5 |
| 4,420,428 | 12/1983 | Varma | 260/397.45 |
| 4,427,592 | 1/1984 | Varma et al. | 260/397.45 |

OTHER PUBLICATIONS

J. Med. Chem., vol. 26, p. 78, "Novel 17α-Chloro-17-β-sulfinyl Steroids as Specific Inhibitors of Sebaceous Gland Activity: Potential Antiacne Agents", Green et al.

Primary Examiner—Elbert L. Roberts
Attorney, Agent, or Firm—Lawrence S. Levinson; Donald J. Barrack

[57] ABSTRACT

Antiinflammatory activity is exhibited by steroids having the formula

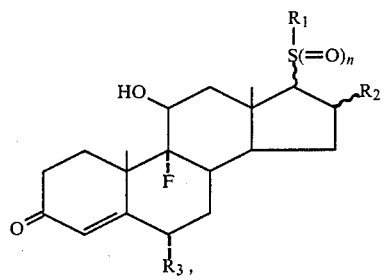

or the 1,2-dehydro derivative thereof, wherein
$R_1$ is alkyl, alkanoyloxyalkyl, arylcarbonyloxyalkyl, alkenyl, alkynyl, cycloalkyl, aryl or arylalkyl;
$R_2$ is hydrogen, hydroxy, alkoxy, aryloxy, methylene, alkylthio, arylthio, alkanoyl, alkanoyloxy, or halogen;
$R_3$ is hydrogen, methyl, hydroxy or halogen; and
$n$ is 0, 1 or 2.

22 Claims, No Drawings

17β-(SUBSTITUTED THIO)ANDROSTENES

BACKGROUND OF THE INVENTION

The disclosures of U.S. Pat. Nos. 4,091,036, issued May 23, 1978, 4,094,840, issued June 13, 1978, 4,133,811, issued Jan. 9, 1979, 4,146,538, issued Mar. 27, 1979, 4,265,815, issued May 5, 1981 and 4,397,782, issued Aug. 9, 1983, encompass within their combined disclosures androstene intermediates having the partial structural formula

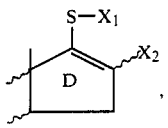

wherein $X_1$ is alkyl, aryl, arylalkyl, or acyloxyalkyl and $X_2$ is chloro, bromo, alkoxy, aryloxy, alkylthio or arylthio.

U.S. Pat. No. 4,361,559, issued Nov. 30, 1982 discloses androstene intermediates having the partial structural formula

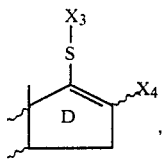

wherein $X_3$ is alkyl, cycloalkyl or aryl, and $X_4$ is hydrogen, hydroxy, alkoxy, aryloxy, alkylthio, arylthio, alkanoyloxy or halogen.

U.S. Pat. No. 4,420,428, issued Dec. 13, 1983 discloses androstene intermediates having the partial structural formula

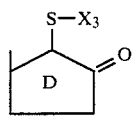

wherein $X_3$ is alkyl, cycloalkyl or aryl.

U.S. Pat. No. 4,427,592, issued Jan. 24, 1984 discloses androstene intermediates having the partial structural formula

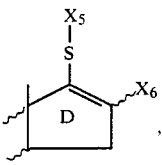

wherein $X_5$ is alkyl, aryl, arylalkyl, cycloalkyl, alkenyl, substituted alkenyl, alkynyl, substituted alkynyl, mono-, di-, or trifluoroalkyl, cyanoalkyl, alkanoylalkyl or

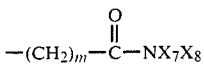

wherein m is 1, 2, 3 or 4 and $X_7$ and $X_8$ are hydrogen or alkyl, and $X_6$ is hydrogen, hydroxy, alkoxy, aryloxy, oxo, methylene, alkylthio, arylthio, alkanoyl, alkanoyloxy or fluorine.

U.S. Pat. No. 4,183,924, issued Jan. 15, 1980, discloses 11-ketoandrostene products (anti-acne agents) having the partial structural formula

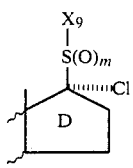

wherein m is 1 or 2 and $X_9$ is benzyl, phenethyl, methylbenzyl, dimethylbenzyl, or chlorobenzyl and an alkyl group, and as intermediates, 11-ketoandrostenes having the partial structural formula

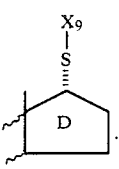

Green et al., in *J. Med. Chem.*, 26(1):78 (1983), discloses an 11β-hydroxy-androstene having the partial structural formula

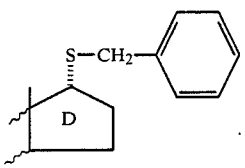

BRIEF DESCRIPTION OF THE INVENTION

Steroids having the formula

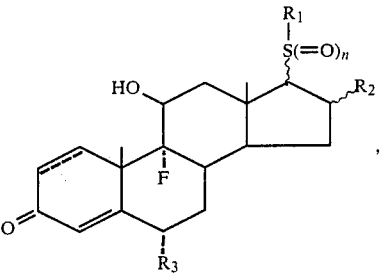

have topical antiinflammatory activity. In formula I, and throughout the specification, the symbols are as defined below.

$R_1$ is alkyl, alkanoyloxyalkyl, arylcarbonyloxyalkyl, alkenyl, alkynyl, cycloalkyl, aryl or arylalkyl;

$R_2$ is hydrogen, hydroxy, alkoxy, aryloxy, methylene (=CH$_2$), alkylthio, arylthio, alkanoyl, alkanoyloxy, or halogen;

$R_3$ is hydrogen, methyl, hydroxy, alkanoyl or halogen; and n is 0, 1 or 2.

The dotted line in the 1,2-positions of the structural formulas shown in this specification indicate the optional presence of ethylenic unsaturation.

The term "aryl", as used throughout the specification either individually or as part of a larger group, refers to phenyl or phenyl substituted with one, two or three alkyl, alkoxy or halogen groups.

The term "halogen", as used throughout the specification either individually or as part of a larger group, refers to fluorine, chlorine, bromine and iodine.

The terms "alkyl" and "alkoxy", as used throughout the specification either individually or as part of a larger group, refer to groups having 1 to 12 carbon atoms.

The terms "alkanoyl", "alkenyl" and "alkynyl", as used throughout the specification either individually or as part of a larger group, refer to groups having 2 to 13 carbon atoms.

DETAILED DESCRIPTION OF THE INVENTION

The steroids of formula I, and the 1,2-dehydro and 6,7-dehydro derivatives thereof, are topical antiinflammatory agents that can be used to treat skin conditions such as dermatitis, psoriasis, sunburn, eczema, neurodermatitis, or anogenital pruritus, and inhalation therapy for topical treatment of allergy and asthma.

For the treatment of skin conditions, the topical antiinflammatory steroids of this invention may be administered in a conventional pharmaceutical carrier in the form of a cream, ointment, lotion or the like. The steroids will preferably be used in the range of 0.01 to 5.0% by weight of the vehicle, preferably 0.05 to 2.0% by weight of the vehicle.

For the topical treatment of allergy and asthma the topical antiinflammatory steroids of this invention may be administered in the conventional manner, e.g., as solid medicament which has been atomized. U.S. Pat. Nos. 3,948,264 and 4,147,166, are exemplary of the literature which describes devices that can be used to administer solid medicaments for inhalation therapy.

The steroids of formula I having a 17β-substituent can be prepared from the corresponding androstene having the formula

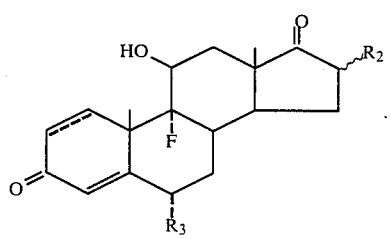

II

The androstenes of formula II are well known in the art; see, for example, U.S. Pat. No. 4,361,559, issued Nov. 30, 1982.

Reaction of an androstene of formula II with hydrogen sulfide in the presence of an organic amine such as morpholine yields the corresponding steroid having the formula

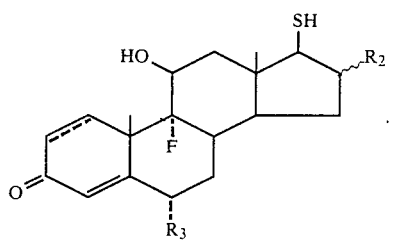

III

The androstenes of formula III are novel intermediates, and as such, constitute an integral part of this invention.

Reaction of an intermediate of formula III with a compound having the formula $$R_1-Y_1, \qquad IV$$

wherein $Y_1$ is a leaving group such as halogen, yields the corresponding product of formula I having a 17β-substituent. The reaction is preferably run in the presence of an inorganic base.

The steroids of formula I having a 17α-substituent can be prepared from the corresponding steroid having the formula

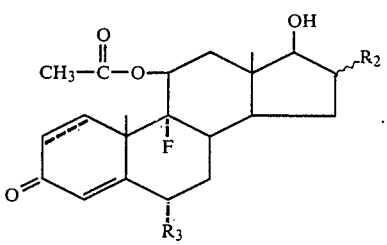

V

Sequential reaction of a steroid of formula V with a phosphine such as triphenylphosphine, an azodicarboxylate such as diethylazodicarboxylate and a thiol having the formula $$R_1-SH \qquad VI$$

yields the corresponding steroid having the formula

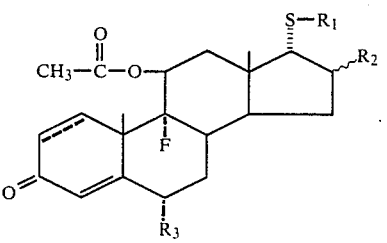

VII

Deprotection using conventional techniques yields the desired product of formula I having a 17α-substituent.

Alternatively, the steroids of formula I having a 17β-substituent can be prepared from an androstene having the formula

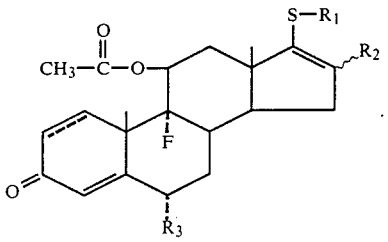

Steroids of formula VIII are known in the art; see, for example, U.S. Pat. Nos. 4,361,559 and 4,427,592. Treatment of a compound of formula VIII with a silane such as triethylsilane and an acid such as trifluoroacetic acid yields the corresponding compound having the formula

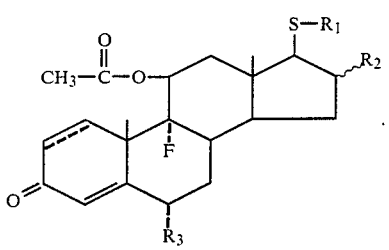

Deprotection of the 11-hydroxy group using conventional techniques yields the desired product of formula I having a 17β-substituent. It is also possible to utilize the 11β-hydroxy analog of a steroid of formula VIII in this reaction.

Alternatively, the steroids of formula I having a 17α-substituent can be prepared by first reacting an androstene of formula V with a compound having the formula

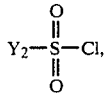

wherein $Y_2$ is alkyl or aryl, to obtain the corresponding steroid having the formula

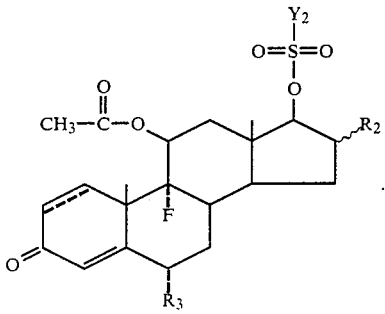

Reaction of a steroid of formula XI with a metal (e.g., sodium) mercaptide prepared from a thiol of formula VI, yields the corresponding product of formula I having a 17α-substituent.

Alternatively, steroids of formula I wherein $R_1$ is alkanoyloxyalkyl or arylcarbonyloxyalkyl can be prepared from the corresponding 17-alkylthio steroid of formula I. Oxidation of the 17-alkylthio steroid with approximately one equivalent of an oxidizing agent such as m-chloroperoxybenzoic acid yields the corresponding 17-alkylsulfinyl steroid. Acylation of the 17-alkylsulfinyl steroid using, for example, an acid anhydride, yields the desired 17-acyloxyalkylthio steroid.

The steroids of formula I wherein n is 1 or 2 can be obtained from the corresponding sulfide of formula I (i.e., n is 0) by oxidizing the sulfide with the appropriate amount of a peracid such as m-chloroperbenzoic acid or periodic acid. The use of about one equivalent of the oxidizing agent yields the sulfoxide (n is 1) and the use of excess oxidizing agent yields the sulfone (n is 2).

Preparation of the starting 17β-hydroxy steroid of formula V is described in copending U.S. patent application Ser. No. 577,444, filed Feb. 6, 1984. Using art-recognized acylation techniques, a steroid of formula II can first be converted to the corresponding 11β-acetyloxy derivative. Reducing an 11β-acetyloxy derivative of a steroid of formula II using, for example, sodium borohydride, yields the desired 17β-hydroxy steroid of formula V.

The following examples are specific embodiments of this invention.

EXAMPLE 1

(11β,17β)-9-Fluoro-11-hydroxy-17-(2-propenylthio)androsta-1,4-dien-3-one (A)

(11β,17β)-9-Fluoro-11-hydroxy-17-mercaptoandrosta-1,4-dien-3-one

Into a chilled solution (ice bath) of 3 g of (11β)-9-fluoro-11-hydroxyandrosta-1,4-dien-3,17-dione in 12 ml of dimethylformamide and 15 ml of morpholine, there was introduced a stream of hydrogen sulfide. Once the exothermic reaction had ceased, the ice bath was removed, the hydrogen sulfide stream was reduced to about one bubble every two seconds and continued overnight. The next day the reaction mixture was poured into ice water, the resulting solid filtered off, washed with water, and dried to yield 3 g of crude product. HPLC analysis indicated the presence of 11% starting material and 88% product. The above 3 g were combined with 2 g of crude product that had been obtained from two earlier batches and chromatographed on silica gel. Elution with chloroform-20% ethyl acetate yielded 2 g of the title compound as a white solid. Crystallization from acetonitrile furnished the analytically pure sample (1.5 g), melting point 295°–297° C. Further elution gave 1 g of the starting steroid. Recrystallization of the thiol from acetic acid yielded needles.

(B)

(11β,17β)-9-Fluoro-11-hydroxy-17-(2-propenylthio)androsta-1,4-dien-3-one

To a stirred solution of 1.7 g of (11β,17β)-9-Fluoro-11-hydroxy-17-mercaptoandrosta-1,4-dien-3-one dissolved in 100 ml of methanol, there was added 1 g of sodium hydroxide followed by 2.5 ml of allyl bromide (nitrogen atmosphere). The alkylation was complete after 1 hour of stirring at room temperature. The solution was partly evaporated, water was added and the resulting solid filtered and washed with water. Crystallization of the solid from ethyl acetate-petroleum ether furnished 1.08 g of the analytical sample, melting point 173°–175° C.

Anal. Calc'd. for $C_{22}H_{29}FO_2S$: C, 70.17; H, 7.76; S, 8.52; F, 5.05. Found: C, 70.08; H, 7.74; S, 8.47; F, 5.07.

EXAMPLE 2

(11β,17α)-9-Fluoro-11-hydroxy-17-(phenylthio)androsta-1,4-dien-3-one (A)

(11β,17α)-11-(Acetyloxy)-9-fluoro-17-(phenylthio)androsta-1,4-dien-3-one

To a magnetically stirred solution of triphenylphosphine (1.05 g) in dry tetrahydrofuran (15.0 ml) maintained at 0° C. was added diethylazodicarboxylate (0.488 ml) and the mixture was stirred at 0° C. for thirty minutes. To this stirred solution at 0° C. was added dropwise, a mixture of (11β,17β)-11-(acetyloxy)-9-fluoro-17-hydroxyandrosta-1,4-dien-3-one (362 mg, 1 mmole) and thiophenol (0.276 ml) dissolved in 5.0 ml of tetrahydrofuran. The solution was added over a ten minute period and then the reaction mixture stirred for 1 hour at 0° C., followed by 5.5 hours at room temperature. TLC (silica gel, 7:3 chloroform:ethyl acetate) indicated very little reaction taking place so the mixture was refluxed under nitrogen for 48.0 hours, followed by quenching in water and extraction with chloroform (4×50 ml). The combined chloroform extracts were dried over anhydrous magnesium sulfate and evaporated to a yellow oil. This was dissolved in a mixture of chloroform and hexane (8:2) and preadsorbed on silica gel. Flash chromatography was performed and the desired product was successfully eluted with (9:1) chloroform:hexane. The product-containing fractions were pooled, evaporated to an oil, taken up in hot ethyl acetate and evaporated to a yellow crystalline material which was vacuum dried.

(B)

(11β,17α)-9-Fluoro-11-hydroxy-17-(phenylthio)androsta-1,4-dien-3-one

To a stirred mixture of (11β,17α)-11-(acetyloxy)-9-fluoro-17-(phenylthio)androsta-1,4-dien-3-one (300 mg) in tetrahydrofuran (12.0 ml) and methanol (6.0 ml) (in a nitrogen atmosphere) was added 1.5 ml of a 12% sodium hydroxide solution. TLC (7:3, chloroform:ethyl acetate) taken after 1 hour showed the reaction to be complete. After a total of 1.5 hours at room temperature, the reaction was quenched with water and extracted with chloroform (3×50 ml). The chloroform extracts were pooled, dried over anhydrous magnesium sulfate and evaporated to a yellow oil. This was dissolved in 10.0 ml of boiling dichloromethane, cooled, and a few drops of petroleum ether were added. The solution was left in the freezer overnight, yielding fine, light green needle-like crystals (57 mg) of an analytical specimen with consistent spectral data and melting point 248°-252° C. (with decomposition).

Anal. Calc'd. for $C_{25}H_{29}O_2SF$: C, 72.78; H, 7.37; S, 7.77; F, 4.61. Found: C, 72.88; H, 7.15; S, 7.67; F, 4.60.

EXAMPLE 3

(11β,17α)-9-Fluoro-11-hydroxy-17-(methylthio)androsta-1,4-dien-3-one (A)

(11β,17β)-11-(Acetyloxy)-9-fluoro-17-(methanesulfonyloxy)androsta-1,4-dien-3-one A solution of (11β,17β)-11-(acetyloxy)-9-fluoro-17-hydroxyandrosta-1,4-dien-3-one (1.0 g; 2.9 mmole) in dry pyridine (12 ml) was stirred in an ice bath and methanesulfonyl chloride (0.435 ml; 644 mg; 5.6 mmoles) was added. The solution was left standing at 0°-5° C. for 20 hours and then poured into ice-cold 20% hydrochloric acid. The mixture was extracted with chloroform, the chloroform solution was washed with water, a dilute sodium bicarbonate solution and water, dried (anhydrous magnesium sulfate) and evaporated to afford a solid (1.20 g). One crystallization from ethyl acetatehexane gave a specimen (1.0 g), melting point 210°-211° C. (dec.), with consistent spectral data.

(B)

(11β,17α)-9-Fluoro-11-hydroxy-17-(methylthio)androsta-1,4-dien-3-one

To a suspension of 50% sodium hydride/paraffin (100 mg) in dry dimethylformamide (10 ml), cooled and stirred in an ice bath, a stream of methanethiol was passed until a homogeneous solution resulted. (11β,17β)-11-(Acetyloxy)-9-fluoro-17-(methanesulfonyloxy)androsta-1,4-dien-3-one (280 mg, 0.64 mmole) was added and the solution was heated in an atmosphere of nitrogen in a bath at 100°-120° C. for 5.0 hours. The mixture was then cooled to room temperature and water (1.0 ml) was added. After stirring for 20 minutes, the mixture was poured into water and was extracted with chloroform. The chloroform solution was washed with water, dried (anhydrous magnesium sulfate) and evaporated in vacuo. The residue was dissolved in chloroform-hexane (7:3; 15 ml) and absorbed on a column of silica gel (5.0 g). The column was first eluted with chloroform to remove the paraffin. Further elution of the column with chloroform: hexane (9:1) gave the title compound (179 mg) which had a small amount of a slightly less polar impurity (tlc). One crystallization of this from ethyl acetate followed by drying (110° C., 0.3 mm of Hg, 20 hours) gave the analytical specimen (157 mg), melting point 235°-236° C. with consistent spectral data.

Anal. Calc'd. for $C_{20}H_{27}FO_2S$: C, 68.53; H, 7.77; F, 5.42; S, 9.15. Found: C, 68.73; H, 7.87; F, 5.45; S, 8.90.

EXAMPLE 4

(11β,17α)-17-(Ethylthio)-9-fluoro-11-hydroxyandrosta-1,4-dien-3-one

A suspension of 50% sodium hydride-paraffin (300 mg, 6.5 mmole) in dry dimethylformamide (20 ml) was cooled and stirred in an ice-water bath and ethanethiol (0.67 ml, 9.0 mmole) was added. The ice bath was then removed and the mixture was stirred at room temperature until a clear solution resulted. Then, (11β,17β)-11-(acetyloxy)-9-fluoro-17-(methanesulfonyloxy)androsta-1,4-dien-3-one (540 mg, 1.21 mmole) was added. The resulting solution was heated in a bath at 110°-120° C. under an atmosphere of nitrogen for 5.0 hours. After cooling to room temperature, water (1.0 ml) was added and the mixture was stirred for 20 minutes. The mixture was then added into water (150 ml) and was extracted with chloroform (3×50 ml). The extracts were combined, washed with water, dried (anhydrous magnesium sulfate) and evaporated to afford the title compound as a solid contaminated with paraffin. It was dissolved in chloroform-hexane (7:3; 20 ml) and absorbed on a column of silica gel (15 g). The column was then successively eluted with chloroform and chloroform:ethyl acetate (85:15) to afford the homogeneous (tlc) title compound as a solid (380 mg) from the later fractions. One crystallization from ethyl acetate-hexane followed by drying (110° C., 0.3 mm of Hg, 6 hours) gave the analytical specimen (362 mg), melting point 196°–197° C. with consistent spectral data.

Anal. Calc'd. for $C_{21}H_{29}FO_2S$: C, 69.19; H, 8.02; F, 5.22; S, 8.80. Found: C, 69.40; H, 8.03; F, 5.33; S, 8.52.

EXAMPLE 5

(11β,17β)-9-Fluoro-11-hydroxy-17-(methylthio)androsta-1,4-dien-3-one

Method I (A)

(11β,17β)-11-(Acetyloxy)-9-fluoro-17-(methylthio)androsta-1,4-dien-3-one

A solution of (11β,17β)-11-(acetyloxy)-9-fluoro-17-(methylthio)androsta-1,4,16-trien-3-one (3.0 g, 7.7 mmole) in dry dichloromethane (60 ml) was stirred with triethylsilane (1.1 g) and dry trifluoroacetic acid (0.9 g) for 2.0 hours. The same amounts of reagents were again added. After 20 hours, the solution was washed with water, a dilute sodium bicarbonate solution and water, dried (anhydrous magnesium sulfate) and evaporated to afford the crude product. One crystallization of this from ethyl acetate-hexane gave the title compound (2.4 g) melting point 169°–170° C., with consistent spectral data.

(B)

(11β,17β)-9-Fluoro-11-hydroxy-17-(methylthio)androsta-1,4-dien-3-one

A solution of (11β,17β)-11-(acetyloxy)-9-fluoro-17-(methylthio)androsta-1,4-dien-3-one (2.0 g; 5.09 mmole) in a mixture of methanol (15 ml) and tetrahydrofuran (15 ml) was flushed well with nitrogen, 3M aqueous sodium hydroxide (2.0 ml) was added and the mixture was stirred at room temperature for 45 minutes. A moderate excess of acetic acid was added, the mixture was concentrated in vacuo and was diluted with water. The steroid that separated was isolated by filtration, washed with water, dried, crystallized from ethyl acetate-hexane and dried (100° C., 0.3 mm of Hg, 10 hours) to afford the homogeneous (tlc) analytical specimen of the title commpound (1.4 g), melting point 269°–270° C. with consistent spectral data.

Anal. Calc'd. for $C_{20}H_{27}FO_2S$: C, 68.53; H, 7.77; F, 5.42; S, 9.15. Found: C, 68.69; H, 7.84; F, 5.28; S, 9.13.

METHOD II

A solution of 1.8 g (5.17 mmole) of 9-fluoro-11β-hydroxy-17-(methylthio)androsta-1,4,16-trien-3-one, 648 mg (5.7 mmole) of dry trifluoroacetic acid and 722 mg (6.2 mmole) of triethylsilane in 100 ml of dry dichloromethane was stirred at room temperature under a nitrogen atmosphere. The tlc of an aliquot after 2.0 hours showed about 60% unreacted starting material. More trifluoroacetic acid (972 mg) and triethylsilane (1.083 g) were added. The reaction was continued for another 2 hours while the starting steroid disappeared (tlc). The resulting solution was diluted with dichloromethane, washed with saturated sodium bicarbonate and water, dried (anhydrous sodium sulfate) and evaporated in vacuo. The residue was redissolved in 1:9 hexane-chloroform and chromatographed on a 30 g silica gel column. Elutions successively with 1:9 hexane-chloroform, chloroform and 5:95 ethyl acetate-chloroform gave 800 mg of the tlc-homogeneous title compound. Crystallization from acetone-hexane gave 455 mg of an analytical specimen, melting point 268°–269° C., with consistent spectral data.

Anal. Calc'd. for $C_{20}H_{27}FO_2S$: C, 68.53; H, 7.77; F, 5.42; S, 9.15. Found: C, 68.72; H, 8.07; F, 5.18; S, 9.21.

EXAMPLE 6

(11β,17β)-17-(Ethylthio)-9-fluoro-11-hydroxyandrosta-1,4-dien-3-one

To a homogeneous solution of 600 mg (1.66 mmole) of 17-(ethylthio)-9-fluoro-11β-hydroxyandrosta-1,4,16-trien-3-one in a mixture of dry dichloromethane (60 ml) and trifluoroacetic acid (207 mg) was added triethylsilane (230 mg) and the mixture was stirred at room temperature under a nitrogen atmosphere for 2.5 hours. Since the tlc of an aliquot showed incomplete reaction, more trifluoroacetic acid (207 mg) and triethylsilane (230 mg) were added. After 1.5 hours the starting material had disappeared by tlc. The resulting solution was diluted with dichloromethane, washed with saturated sodium bicarbonate solution and water, dried (anhydrous sodium sulfate) and evaporated in vacuo to give a solid. This was redissolved in 1:4 hexane chloroform and chromatographed on a 30 g silica gel column. Elution with 1:4 hexane-chloroform, chloroform and 5:95 ethyl acetate-chloroform gave 520 mg of a tlc-homogeneous title compound. Crystallization from acetone-hexane gave 410 mg of an analytical specimen, melting point 223°–225° C., with consistent spectral data.

Anal. Calc'd. for $C_{21}H_{29}FO_2S$: C, 69.19; H, 8.02; F, 5.21; S, 8.80 Found: C, 69.17; H, 7.97; F, 5.16; S, 8.80

EXAMPLE 7

(11β,17β)-9-Fluoro-11-hydroxy-17-(methylsulfinyl)androsta-1,4-dien-3-one

To a solution of (11β,17β)-9-fluoro-11-hydroxy-17-(methylthio)androsta-1,4-dien-3-one (701 mg, 2.0 mmole; see example 5) in chloroform (30 ml) was added a solution of 85% m-chloroperbenzoic acid (398 mg, 2.0 mmole) in chloroform (10 ml). An instantaneous reaction was observed (tlc). The solution was then washed with a 10% potassium carbonate solution and water, dried (anhydrous magnesium sulfate) and evaporated to afford the title compound as a solid (700 mg). One crystallization of this from acetone-hexane followed by drying (100° C., 0.3 mm of Hg, 10 hours) gave the analytical specimen of the title compound (600 mg) melting point 270°–272° C. dec., as a mixture of sulfoxide stereoisomers, with consistent spectral data.

Anal. Calc'd. for $C_{20}H_{27}FO_3S$: C, 65.54; H, 7.42; F, 5.18; S, 8.73. Found: C, 65.69; H, 7.49; F, 5.00; S, 8.87.

EXAMPLE 8

(11β,17β)-21-[[(Acetyloxy)methyl]thio]-9-fluoro-11-hydroxyandrosta-1,4-dien-3-one A mixture of 820 mg (2.24 mmole) of (11β,17β)-9-fluoro-11-hydroxy-17-(methylsulfinyl)androsta-1,4-dien-3-one (see example 7), 45 ml of acetic anhydride and 1.0 g of fused sodium acetate was heated at 100° C. under nitrogen for 3 hours. The solution was cooled and the solvent was evaporated in vacuo at room temperature. The residue was dissolved in chloroform, washed with saturated sodium bicarbonate and water, dried (anhydrous sodium sulfate) and evaporated in vacuo to give a solid (800 mg). This was dissolved in 1:9 hexane:chloroform and chromatographed on a 30 gram-silica gel column. Elutions successively with chloroform, chloroform-ethyl acetate (95:5) and chloroform-ethyl acetate (9:1) gave 430 mg of the tlc homogeneous title compound. A crystallization from acetone-hexane gave 370 mg of an analytical specimen, melting point 178°–179° C., with consistent spectral data.

Anal. Calc'd. for $C_{22}H_{29}FO_4S$: C, 64.68; H, 7.16; F, 4.65; S, 7.85. Found: C, 64.63; H, 7.20; F, 4.52; S, 7.83.

EXAMPLE 9

($11\beta,17\beta$)-17-(Ethylsulfinyl)-9-fluoro-11-hydroxyandrosta-1,4-dien-3-one To a solution of ($11\beta,17\beta$)-17-(ethylthio)-9-fluoro-11-hydroxyandrosta-1,4-dien-3-one (700 mg, 1.92 mmole; see example 6) in chloroform (30 ml) was added a solution of 86% m-chloroperbenzoic acid (390 mg, 1.95 mmole) in chloroform (15 ml). An instantaneous reaction was noted (tlc). The solution was then washed with a 10% potassium carbonate solution and water, dried (anhydrous magnesium sulfate) and evaporated to afford the title compound (697 mg) as a solid. One crystallization of this from ethyl acetate followed by drying (100° C., 0.3 mm of Hg, 10 hours) gave the analytical specimen of the title compound (600 mg), melting point 247°–250° C., with consistent spectral data.

Anal. Calc'd. for $C_{21}H_{29}FO_3S$: C, 66.28; H, 7.68; F, 4.99; S, 8.41. Found: C, 66.40; H, 7.59; F, 4.92; S, 8.37.

What is claimed is:

1. A steroid having the formula

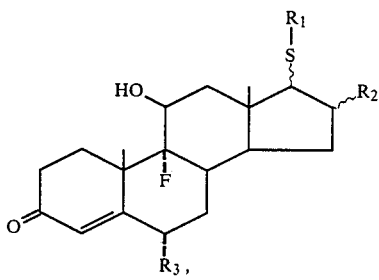

or the 1,2-dehydro derivative thereof, wherein
$R_1$ is alkyl, alkanoyloxyalkyl, arylcarbonyloxyalkyl, alkenyl, alkynyl, cycloalkyl, aryl or arylalkyl;
$R_2$ is hydrogen, hydroxy, alkoxy, aryloxy, methylene, alkylthio, arylthio, alkanoyl, alkanoyloxy, or halogen; and
$R_3$ is hydrogen, methyl, hydroxy or halogen.

2. A steroid in accordance with claim 1 wherein $R_2$ is hydrogen.

3. A steroid in accordance with claim 1 wherein $R_3$ is hydrogen.

4. A steroid in accordance with claim 1 wherein $R_1$ is alkyl.

5. A steroid in accordance with claim 1 wherein $R_1$ is alkenyl.

6. A steroid in accordance with claim 1 wherein $R_1$ is alkanoyloxyalkyl.

7. A steroid in accordance with claim 1 wherein $R_1$ is arylcarbonyloxyalkyl.

8. A steroid in accordance with claim 1 wherein $R_1$ is alkynyl.

9. A steroid in accordance with claim 1 wherein $R_1$ is cycloalkyl.

10. A steroid in accordance with claim 1 wherein $R_1$ is aryl.

11. A steroid in accordance with claim 1 wherein $R_1$ is arylalkyl.

12. The steroid in accordance with claim 1, ($11\beta,17\beta$)-9-fluoro-11-hydroxy-17-(2-propenylthio)androsta-1,4-dien-3-one.

13. The steroid in accordance with claim 1, ($11\beta,17\alpha$)-9-fluoro-11-hydroxy-17-(phenylthio)androsta-1,4-dien-3-one.

14. The steroid in accordance with claim 1, ($11\beta,17\alpha$)-9-fluoro-11-hydroxy-17-(methylthio)androsta-1,4-dien-3-one.

15. The steroid in accordance with claim 1, ($11\beta,17\alpha$)-17-(ethylthio)-9-fluoro-11-hydroxyandrosta-1,4-dien-3-one.

16. The steroid in accordance with claim 1, ($11\beta,17\beta$)-9-fluoro-11-hydroxy-17-(methylthio)androsta-1,4-dien-3-one.

17. The steroid in accordance with claim 1, ($11\beta,17\beta$)-17-(ethylthio)-9-fluoro-11-hydroxyandrosta-1,4-dien-3-one.

18. A steroid having the formula

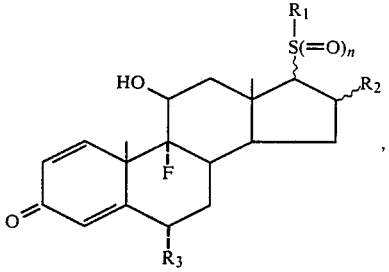

wherein
$R_1$ is alkyl, alkanoyloxyalkyl, arylcarbonyloxyalkyl, alkenyl, alkynyl, cycloalkyl, aryl or arylalkyl;
$R_2$ is hydrogen, hydroxy, alkoxy, aryloxy, methylene, alkylthio, arylthio, alkanoyl, alkanoyloxy, or halogen;
$R_3$ is hydrogen, methyl, hydroxy or halogen; and
$n$ is 0, 1 or 2.

19. The steroid in accordance with claim 18, ($11\beta,17\beta$)-17-(ethylsulfinyl)-9-fluoro-11-hydroxyandrosta-1,4-dien-3-one.

20. The steroid in accordance with claim 18, ($11\beta,17\beta$)-9-fluoro-11-hydroxy-17-(methylsulfinyl)androsta-1,4-dien-3-one.

21. A steroid having the formula

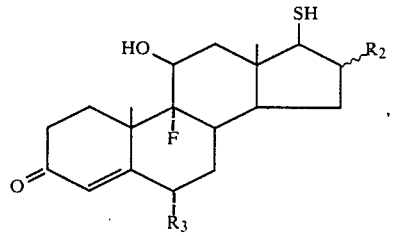

or the 1,2-dehydro derivative thereof, wherein
$R_2$ is hydrogen, hydroxy, alkoxy, aryloxy, methylene, alkylthio, arylthio, alkanoyl, alkanoyloxy, or halogen; and
$R_3$ is hydrogen, methyl, hydroxy or halogen.

22. The steroid in accordance with claim 19, ($11\beta,17\beta$)-9-fluoro-11-hydroxy-17-mercaptoandrosta-1,4-dien-3-one.

* * * * *